(12) United States Patent
McEwen et al.

(10) Patent No.: US 8,758,390 B2
(45) Date of Patent: Jun. 24, 2014

(54) TOURNIQUET EFFECTOR

(75) Inventors: James A. McEwen, Vancouver (CA); Michael Jameson, North Vancouver (CA); Michael A. Gebert, Wetminster (CA)

(73) Assignee: Western Clinical Engineering, Ltd. CA (US)

( * ) Notice: Subject to any disclaimer, the term of this patent is extended or adjusted under 35 U.S.C. 154(b) by 222 days.

(21) Appl. No.: 13/083,153

(22) Filed: Apr. 8, 2011

(65) Prior Publication Data

US 2011/0251636 A1    Oct. 13, 2011

Related U.S. Application Data

(60) Provisional application No. 61/323,486, filed on Apr. 13, 2010.

(51) Int. Cl.
*A61B 17/00* (2006.01)

(52) U.S. Cl.
USPC ........................................ 606/203

(58) Field of Classification Search
USPC ................................ 606/201–203
See application file for complete search history.

(56) References Cited

U.S. PATENT DOCUMENTS

| | | | |
|---|---|---|---|
| 4,469,099 A | 9/1984 | McEwen | |
| 4,479,494 A | 10/1984 | McEwen | |
| 5,181,522 A * | 1/1993 | McEwen | 600/561 |
| 5,307,811 A * | 5/1994 | Sigwart et al. | 600/490 |
| 5,352,195 A | 10/1994 | McEwen | |
| 5,439,477 A | 8/1995 | McEwen | |
| 5,503,156 A | 4/1996 | Millar | |
| 5,554,168 A * | 9/1996 | Petersen | 606/201 |
| 5,556,415 A | 9/1996 | McEwen | |
| 5,643,315 A | 7/1997 | Daneshvar | |
| 5,855,589 A | 1/1999 | McEwen | |
| 5,911,735 A | 6/1999 | McEwen | |
| 6,176,831 B1 | 1/2001 | Voss | |
| 6,746,470 B2 | 6/2004 | McEwen | |
| 2004/0267123 A1 | 12/2004 | McMorrow | |
| 2005/0075568 A1 | 4/2005 | Moehring | |
| 2007/0191881 A1* | 8/2007 | Amisar et al. | 606/203 |

FOREIGN PATENT DOCUMENTS

| | | |
|---|---|---|
| WO | 2007069155 | 6/2007 |
| WO | 2009012594 | 1/2009 |

* cited by examiner

*Primary Examiner* — Tuan V Nguyen
(74) *Attorney, Agent, or Firm* — Hancock Hughey LLP

(57) ABSTRACT

Tourniquet effector system estimates and indicates the pressure gradients produced on the surface of the body by an effector, thereby allowing the pressure gradients to be minimized. The system also detects and monitors blood flow beneath the effector, thereby allowing the pressure applied by the effector to be regulated near the minimum necessary to stop blood flow past the effector.

15 Claims, 6 Drawing Sheets

TOURNIQUET EFFECTOR

FIELD OF THE INVENTION

This invention pertains to a tourniquet effector for safely stopping the flow of arterial blood in a region of a body in order to reduce morbidity and mortality, or to facilitate the performance of a surgical procedure.

BACKGROUND OF THE INVENTION

Tourniquet systems are commonly used in limb surgery. Typical surgical tourniquet systems of the prior art include a tourniquet cuff which encircles the limb of a surgical patient and a tourniquet instrument which is releasably connected to an inflatable portion within the tourniquet cuff through a length of tubing, thereby establishing a gas-tight passageway between the cuff and the tourniquet instrument. The tourniquet instrument supplies pressurized gas to inflate and regulate the pressure in the tourniquet cuff above a minimum pressure required to stop arterial blood flow distal to the cuff, for a duration suitably long for the performance of a surgical procedure. Many types of surgical tourniquet systems have been described in the prior art, such as those described by McEwen in U.S. Pat. Nos. 4,469,099, 4,479,494, 5,439,477 and McEwen and Jameson in U.S. Pat. Nos. 5,556,415 and 5,855,589.

Tourniquet systems are increasingly used in pre-surgical settings to stop arterial blood flow and thereby reduce blood loss, morbidity and mortality. For example, specialized emergency and military tourniquets based on apparatus described by McEwen et al in U.S. Pat. No. 6,746,470 have been used in combat settings, field hospitals and in civilian pre-hospital settings. In comparison to earlier, non-pneumatic device of the prior art, the pneumatic tourniquet apparatus described by McEwen et al in U.S. Pat No. 6,746,470, reduces unnecessary injuries by reducing the pressure levels and pressure gradients required to stop arterial blood flow in limbs reliably and safely.

Typically, tourniquet cuffs of the prior art encircle a patient's limb at a desired location. Studies published in the surgical literature have shown that the safest tourniquet inflation pressure is the lowest pressure that will stop the flow of arterial blood past a specific tourniquet cuff applied to a specific patient for the duration of that patient's surgery. Such studies have shown that higher tourniquet inflation pressures are associated with higher risks of tourniquet-related injuries to the patient.

It has been also been shown in the published literature that higher pressure gradients are associated with higher probabilities of injuries. Pressure gradients are produced on limbs beneath tourniquet cuffs and extend across the width of the cuffs. Variables that affect pressure gradients produced on limbs by encircling pneumatic tourniquet cuffs include: cuff width; cuff design and materials; characteristics of any stiffening element or means within the cuff; shape and size of any inflatable region of the cuff; degree of match between the shape of the limb and shape of the encircling cuff; and the inflation pressure level employed to stop blood flow. Typically, tourniquet cuffs of the prior art have only been useful when a sufficient width of a patient's limb is available for the application of the tourniquet cuff so that it can encircle the limb and overlap upon itself. However, there are many situations in which there is a need to reliably and safely stop arterial blood flow and in which the use of prior-art tourniquet cuffs is not possible. For example, prior-art encircling tourniquet cuffs may not safely and reliably stop arterial blood flow in the limbs of short and obese patients. Other situations include certain traumatic injuries to the proximal portions of limbs that leave insufficient room for application of a prior-art tourniquet cuff, and situations in which traumatic injuries to limbs would extend beneath a prior-art tourniquet cuff if applied. In addition, for certain surgical procedures not involving limbs, there is a need for apparatus that can selectively stop arterial blood flow in order to facilitate surgery, to reduce surgical precision and time, to increase safety and to improve long-term surgical outcomes. Such procedures include surgery of the hip, surgery of the shoulder and abdominal surgery. For a variety of procedures performed on limbs, there is a need for apparatus which could safely and reliably stop blood flow in selected arteries, rather than stopping all blood flow in all vessels that would otherwise underlie an encircling prior-art tourniquet cuff. The present invention addresses these needs.

DETAILED DESCRIPTION OF THE PREFERRED EMBODIMENT

The specific embodiment illustrated is not intended to be exhaustive or to limit the invention to the precise form disclosed. It is chosen and described in order to explain the principles of the invention and its application and practical use, and thereby enable others skilled in the art to utilize the invention.

Figure 1:
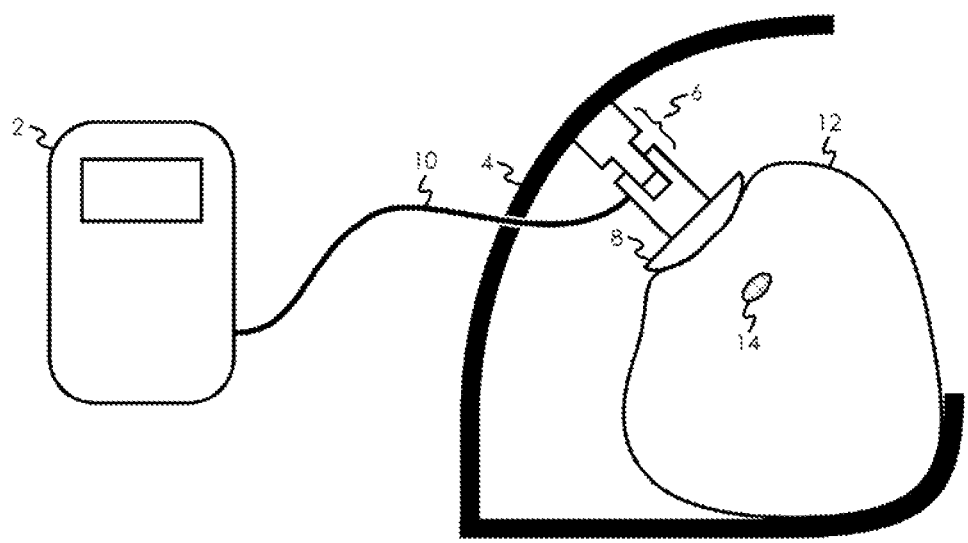
FIG. 1 is a cross-section view of the preferred embodiment.

A tourniquet effector system is shown in cross-section in FIG. 1 and consists of: controller 2, fixture 4, actuator 6 and effector 8. Controller 2 communicates with actuator 6 and effector 8 via cable 10. Alternatively, controller 2 may communicate with actuator 6 and effector 8 via a wireless radio link. Controller 2 includes a user interface that permits a user to control the operation of the tourniquet effector system and that displays relevant information regarding the operation of the tourniquet effector system to the user. Controller 2 displays the following information to a user of the tourniquet effector system: estimates of the pressures applied by effector 8 to the body surface; estimates of the pressure gradients produced on the body surface by effector 8; information regarding the flow and penetration of arterial blood in the tissues underlying effector 8; and warning and alerts if pressure gradients, applied pressures or blood flows exceed either predetermined limits or limits set by a user of the tourniquet effector system. The user interface of controller 2 permits a user of the tourniquet effector system to: set reference levels for the pressure to be applied by effector 8 and pressure gradients to be produced by effector 8; set alarm limits for applied pressures and gradients produced by effector 8, set reference levels and alarm limits for the penetration of arterial blood and blood flow beneath effector 8.

Effector 8 applies pressure to a patient's body surface 12 to close an underlying artery 14. Effector 8 has a back face for attaching to actuator 6 and a front face for applying pressure to the body surface. In order to effectively close underlying artery 14 the width of the front face of effector 8 is greater than the diameter of underlying artery 14. To minimize the risk of nerve and tissue injury when occluding underlying artery 14 the shape and contours of the front face of effector 8 are predetermined to minimize the pressure gradient(s) (rate of change of pressure) produced on the body surface 12 by the front face of effector 8. High pressure gradients on the body surface can cause tissue and nerve damage in the region underlying effector 8.

Pressure is applied by an effector to the area of the body surface that is in contact with the effector, no pressure is applied beyond the perimeter of the effector. The width, area and shape of an effector are factors that affect the pressure gradients produced by the effector on the body surface when force is applied to the effector. A pressure gradient produced by an effector can be estimated by direct measurement with one or more applied pressure sensors as described below. A pressure gradient produced by an effector can also be estimated indirectly if the force applied to the effector and the physical characteristics of the effector are known.

Figure 2:
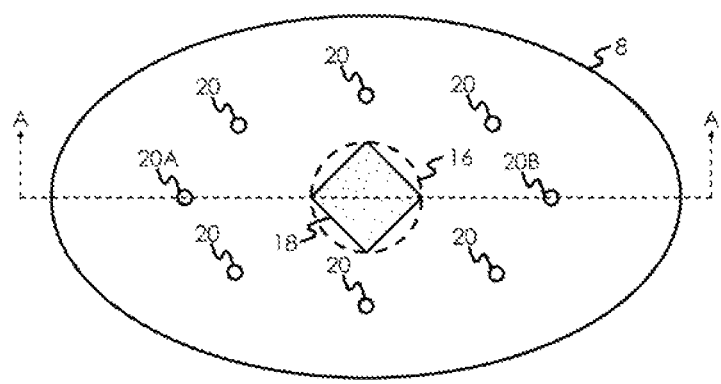
FIG. 2 is view of the body surface contact face of the effector of the preferred embodiment.

As shown in FIG. 2 and described further below effector 8 has pressure sensors at predetermined locations on the front face of effector 8 and at other locations within effector 8 that indicate the pressure applied by the front face of effector 8 to the surface of the body. The pressure sensors produce signals indicative of the pressure sensed that are communicated to controller 2 via cable 10.

Controller 2 estimates the pressure gradients produced by the front face of effector 8 on the body surface using some or all of the following parameters: the total force applied to effector 8 by actuator 6; applied pressure measurements from selected predetermined locations on the front face of effector 8; stored information describing the shape and properties of the materials that comprise effector 8; and stored information describing the properties and compressibility of the body tissues that underlie effector 8.

To estimate the pressure gradients on the body surface underlying effector 8 controller 2 may use: a lookup table of data derived from previous experimentation and measurement of pressure applied the effector to the surface of various regions of the body; a mathematical model to estimate the pressure applied by the effector; calculation using the force applied to the effector by the actuator and the physical characteristics of the effector face; simple calculation using applied pressure measurements from known locations on the face of effector 8; or other techniques known in the prior art.

Fixture 4 provides a frame of reference relative to a patient's the body surface so that effector 8 can apply pressure to the body surface and acts to maintain effector 8 and actuator 6 in position above a selected location on body surface 12. For clarity fixture 4 is illustrated in FIG. 1 as a rigid clamp like structure, alternatively fixture 4 may be any structure that provides a frame of reference relative to the body surface to which the effector is to apply pressure, such as a garment or body armor worn by the patient; a harness or strap applied around the patient's body or any other suitable structure.

Actuator 6 is attached to fixture 4 and the back face of effector 8. Actuator 6 in response to control signals from controller 2 extends to apply force to the back face of effector 8 to press effector 8 against body surface 12 at a selected location to close an underlying artery 14.

In the preferred embodiment as shown in FIG. 1 actuator 6 has a single degree of freedom and is an electric motor driven linear actuator that extends to apply force to effector 8. Actuator 6 responds to control signals from controller 2 to apply a selected amount of force to effector 8. By regulating the force applied by actuator 6 controller 2 can maintain the pressure applied by effector 8 and the pressure gradients produced by effector 8 on the body surface near previously established reference levels.

Other types of controllable linear actuators with a single degree of freedom such as pneumatic or hydraulic cylinders may also be used to apply a chosen amount of force to effector 8. Alternatively, actuator 6 may be selected to have multiple degrees freedom so that both the direction and magnitude of force applied to effector 8 may be varied by controller 2 to affect the pressure gradients produced by the front face of effector 8 at the body surface. In some circumstances, such as when an artery is to be closed temporarily, automatic control of actuator 6 may not be required, and force may be applied to effector 8 manually by the user of the tourniquet effector system.

FIG. 2 is a view of the front (body surface contact) face of effector 8. As shown in FIG. 2, the front face of effector 8 includes a two-dimensional ultrasound transducer array 16 located near the center of the effector. Pressure sensor 18 is positioned behind ultrasound transducer array 16 and indicates the pressure applied to body surface 12 by the face of ultrasound transducer array 16. Multiple additional pressure sensors 20 are positioned at various predetermined locations on the front face of effector 8. The pressure sensors measure the pressure applied by the front face effector 8 to the body surface at the predetermined locations. FIG. 2 depicts eight applied pressure sensors 20, it will be appreciated that a greater or lesser number of sensors may be used depending upon the size and shape of effector 8. For clarity only the operation of pressure sensors 20A, 18 and 20B located at points along cross-section line A-A will be described further below.

Figure 3A:
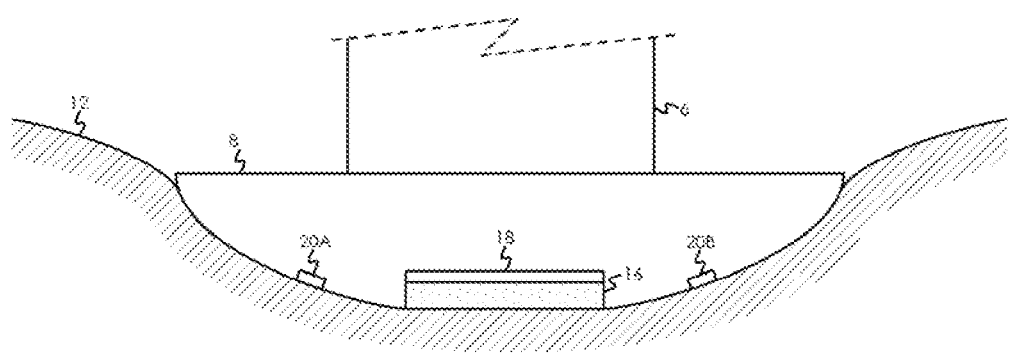
FIG. 3A is cross-section view of the effector applied normal to a body surface.
Figure 3B:
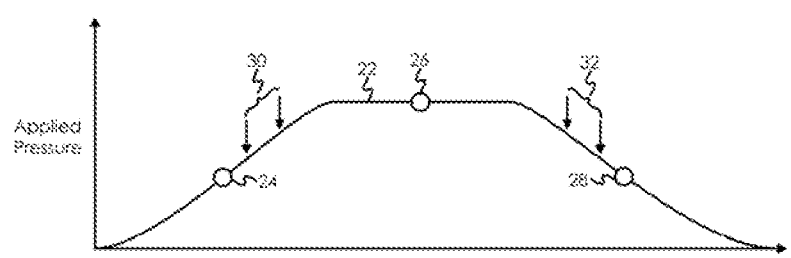
FIG. 3B is a graph of the pressure applied by the effector shown in FIG. 3A.

FIG. 3A is a cross-section view of effector 8 corresponding to cross-section line A-A in FIG. 2. Effector 8 is shown in FIG. 3A normal to body surface 12 applying pressure to close an underlying artery. FIG. 3B is graph corresponding to FIG. 3A of the estimated pressure applied by the front face of effector 8 to body surface 12 at cross-section A-A.

Referring the FIG. 3B, line 22 represents the magnitude of the pressure applied by the front face of effector 8 to body surface 12 at cross-section A-A as estimated by controller 2. Pressure measurements from pressure sensors 20A, 18 and 20B are shown at points 24, 26 and 28 respectively. Controller 2 uses information known about: the shape of the front face of effector 8; the properties of the materials comprising effector 8; the characteristics of the underlying tissue; the force applied to effector 8 by actuator 6; and measurements of the pressure applied by the front face of effector 8 at selected locations to estimate the pressure gradients applied to body surface 12 at other locations on the face of effector 8. As show on the graph in FIG. 3B the front face of effector 8 produces the highest pressure gradients at locations 30 and 32 approximately midway between the centre and outer edge of the front face of effector 8. Controller 2 monitors the pressure gradients produced by effector 8 on the body surface and provides an indication to the user of the tourniquet effector system of those gradients. If the pressure gradient produced at any location on the body surface underlying effector 8 exceeds a maximum gradient limit controller 2 will alert the user and may also act to limit the force applied by actuator 6 to the back face of effector 8 to maintain the pressure gradients produced by the front face of effector 8 at a level below the maximum gradient limit. The maximum gradient limit may be predetermined or set by a user of the tourniquet effector system.

Figure 4A:
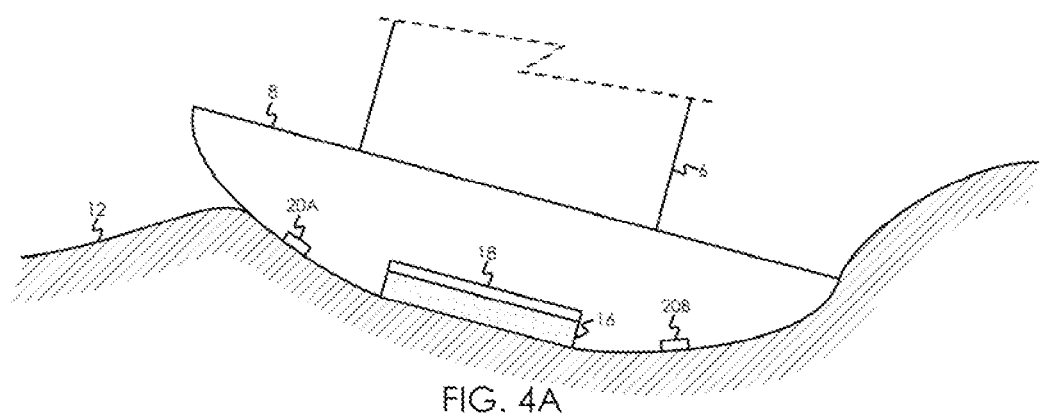
FIG. 4A is cross-section view of the effector when applied at tangent to a body surface.
Figure 4B:
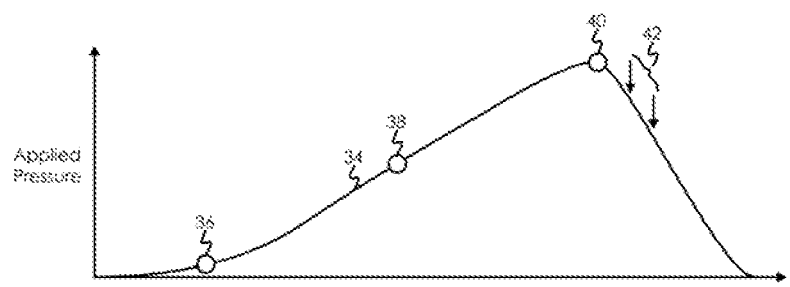
FIG. 4B is a graph of the estimated pressure gradient applied by the effector shown in FIG. 4A.

FIG. 4A depicts effector 8 applied at a tangent to body surface 12 to close an underlying artery. In this example the pressure gradient applied to the body surface in a region of the front face of effector 8 exceeds the maximum gradient limit. The corresponding graph of the pressure applied to body surface 12 as estimated by controller 2 by the front face of effector 8 at cross-section line A-A is shown in FIG. 4B. Pressure measurements from pressure sensors 20A, 18 and 20B are shown on line 34 at points 36, 38 and 40 respectively. The pressure gradient produced by the front face of effector 8 near the right side edge indicated by segment 42 of line 34 exceeds the predetermined maximum gradient threshold. Controller 2 provides an indication to the user that the maximum gradient threshold as been exceeded so that the user may take appropriate action such as reducing the total force applied to effector 8, changing the orientation of effector 8 relative to the body surface, or selecting an effector with a different shape.

Figure 5A:
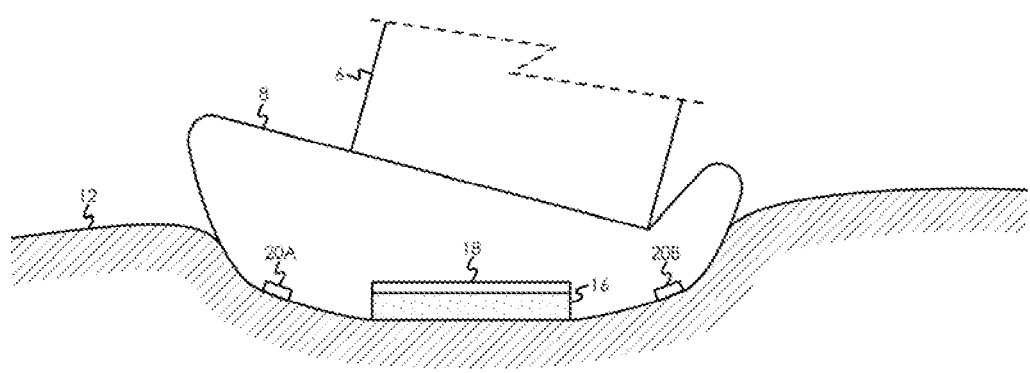
FIG. 5A is cross-section view of the effector adapted to apply minimal pressure gradients when applied at tangent to a body surface.
Figure 5B:
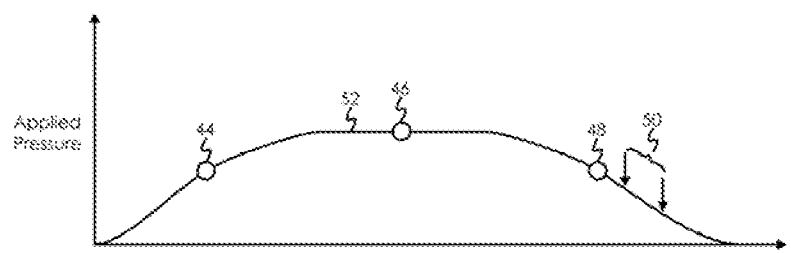
FIG. 5B is a graph of the estimated pressure gradient applied by the effector shown in FIG. 5A.

To illustrate how the shape of the face of effector 8 can be modified to minimize pressure gradients, FIG. 5A depicts effector 8 with an alternate shaped front face applied at a tangent to body surface 12. This alternate shape of the front face of effector 8 has been designed to minimize the pressure gradients applied to body surface 12. The corresponding graph of the pressure applied by a cross-section of the alternate front face of effector 8 as estimated by controller 2 is shown in FIG. 5B. Referring to FIG. 5B, pressure measurements from pressure sensors 20A, 18 and 20B are shown at points 44, 46 and 48 respectively. The pressure gradient produced by the front face of effector 8 near the right side edge indicated by segment 50 of line 52 has been substantially reduced when compared to segment 42 of line 34 in FIG. 4B.

In the examples described above the shape of the front face of effector 8 is predetermined. Alternatively the front face of the preferred embodiment may have a physical shape that can be varied in response to control signals from controller 2 to automatically reduce pressure gradients produced by the effector on the body surface. An alternate effector may include actuators, shape changing materials such as electrorheological materials and other recently developed materials that change shape or prosperities in response to an electric current that are configured to adjust the shape of the face of the effector dynamically in response to sensed applied pressures and estimated pressure gradients.

Figure 6A:
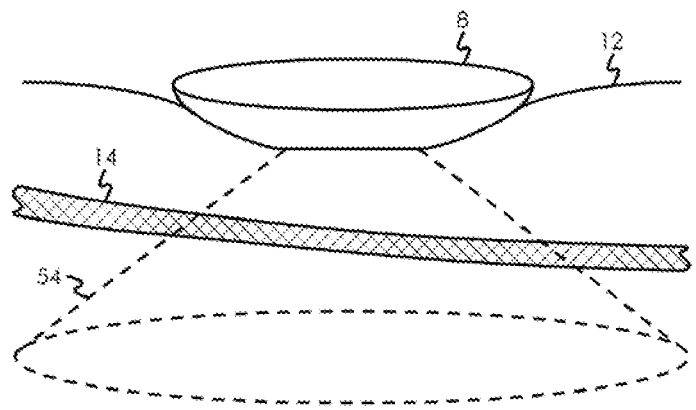
FIG. 6A is an illustration showing an artery beneath the effector and the scanning region of an ultrasound transducer that forms part of the effector.
Figure 6B:
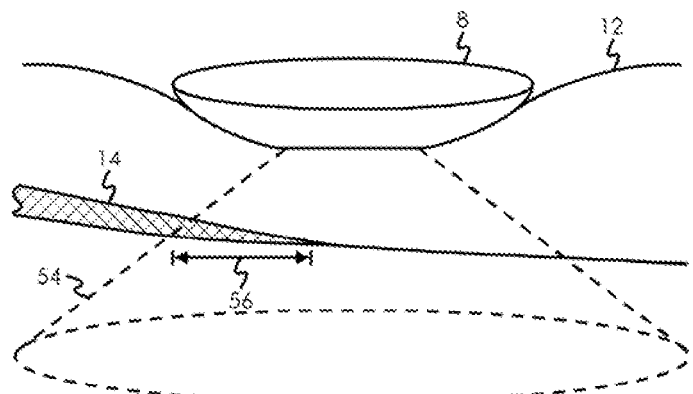
FIG. 6B is an illustration showing a closed artery beneath the effector and the distance that arterial blood penetrates into the scanning region.
Figure 6C:
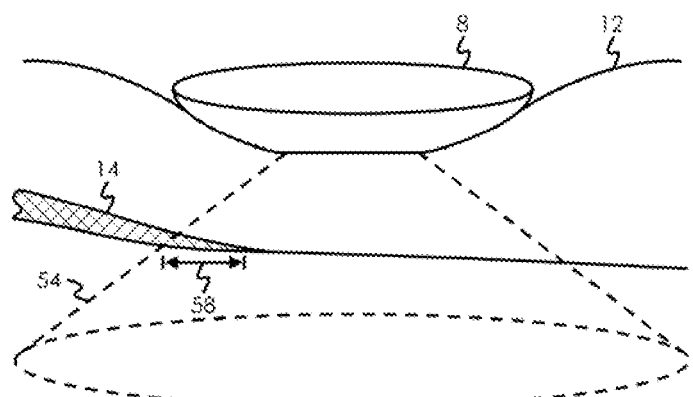
FIG. 6C is an illustration showing a closed artery beneath the effector and the distance that arterial blood penetrates into the scanning region.

Effector 8 includes a two-dimensional ultrasound transducer array 16 positioned near the center of effector 8. Ultrasound transducer array 16 is used by the tourniquet effector system to detect arteries in tissues underlying effector 8 and the extent to which they are closed. As shown in FIGS. 6A, 6B and 6C controller 2 operates ultrasound transducer array 16 to scan a region of tissue underlying effector 8, the region of tissue scanned by ultrasound transducer 16 is indicated by dashed line 54.

Ultrasonic sound waves are emitted by ultrasound transducer 16 at scanning angles relative to front face of effector 8 and traverse the tissue beneath effector 8. The waves emitted by ultrasound transducer 16 reflect off various tissue structures within the underlying tissue. Variations in the amplitude of the reflections allow different tissue structures to be identified, such as the walls of arteries. Doppler frequency shifts in the reflections indicate moving structures, such as the walls of arteries responding to blood pressure variations during cardiac cycles, and blood cells moving within arteries.

Controller 2 operates ultrasound transducer 16 to identify and locate arteries within the tissues beneath effector 8 that are inside the scanning region of the transducer. The lumen minimum diameters of the identified arteries are estimated at locations along their length within the scanning region of ultrasound transducer 16. At the location along the length of an identified artery where the lumen diameter is estimated to be zero, the artery is closed. Arterial blood can penetrate into the tissues beneath effector 8 to the location where the arteries carrying the blood become closed. The location of ultrasound transducer 16 relative to the front face of effector 8 permits the distance that arterial blood penetrates beneath effector 8 to be estimated. The distance of arterial blood penetration is the greatest distance measured relative to the edge of the scanning region that blood penetrates within the arterial vessels underlying effector 8 within one cardiac cycle.

FIGS. 6A, 6B and 6C illustrate the effect that pressure applied to body surface 12 by effector 8 has on the distance of arterial blood penetration beneath effector 8.

FIG. 6A illustrates effector 8 in contact with body surface 12 but applying insufficient pressure to close the underlying artery 14. Blood as indicated by the hatched region within the artery walls is able to flow through artery 14 and penetrate past effector 8.

In FIG. 6B the pressure applied to the body surface by effector 8 has been increased to a level where artery 14 is closed. The distance that blood penetrates into the scanning region of ultrasound transducer 16 and beneath effector 8 is indicated in the figure by line 56.

In FIG. 6C the pressure applied to body surface 12 is greater than that illustrated in FIG. 6B. The increased pressure applied by effector 8 has reduced the distance that blood penetrates into the volume of tissue as indicated by line 58 in the figure.

To minimize the pressure and resulting pressure gradients applied by effector 8 to the body surface 12, controller 2 may be configured to regulate the force applied by actuator 6 to effector 8 to maintain the distance of penetration of arterial blood beneath effector 8 near a desired predetermined maximum distance of penetration. Controller 2 operates to reduce the distance of penetration of arterial blood by increasing the force applied by actuator 6 to effector 8 and to increase the distance of penetration of arterial blood by reducing the force applied to actuator 6. When regulating the force applied by actuator 6 to control the distance of penetration of arterial blood beneath effector 8, controller 2 continues to estimate the pressure gradients produced at the body surface and alerts a user if a pressure gradient exceeds a predetermined maximum gradient limit.

To avoid the high cost complexity of a two dimensional ultrasound transducer array and associated electronics, an alternate lower cost effector and method of detecting blood flow beneath the effector may be used by the tourniquet effector system described above.

Figure 7:
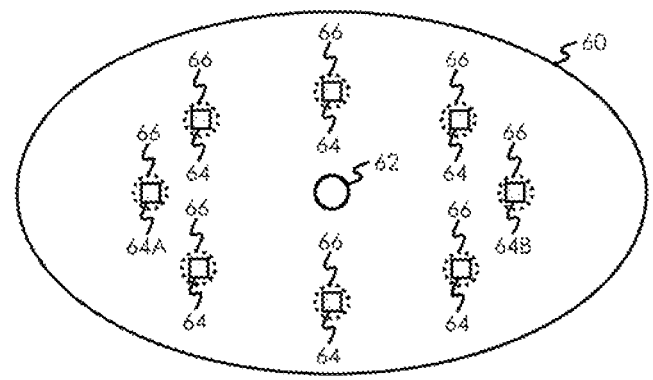
FIG. 7 is view of the body surface contact face of an alternate effector.

FIG. 7 is view of the front face of alternate effector 60. An applied pressure sensor 62 is located near the center of effector 60. A number of single piezoelectric crystal ultrasound sound transducers 64 are located around the perimeter of effector 60. To enable controller 2 to make an accurate estimate of the pressure gradients produced by effector 60, each ultrasound transducer 64 includes a pressure sensor 66 to sense the pressure applied to the body surface by the ultrasound transducer. FIG. 7 depicts eight ultrasound transducers and associated pressure sensors, it will be appreciated that a greater or lesser number of ultrasound transducers may be used depending upon the size and shape of the effector and that applied pressure sensors may be positioned to sense pressure at other locations on the face of the effector. Each ultrasound transducer insonifies a region of tissue beneath effector 60. To detect arterial wall motion and blood flow within the portions of arteries that lie within the region insonified by a transducer, the transducer repeatedly emits ultrasonic sound waves for a short period of time, the waves then reflect off various tissue structures within the insonified tissue and are detected by the same transducer at a later time. Doppler frequency shifts in the reflected sound waves indicate moving structures, such as flowing blood and arterial wall motion. This pulsed Doppler technique may be used to localize regions where arterial blood flow is occurring beneath each transducer. The locations of ultrasound transducers around the perimeter of effector 60 are selected to allow the flow of arterial blood beneath effector 60 to be detected.

Figure 8:
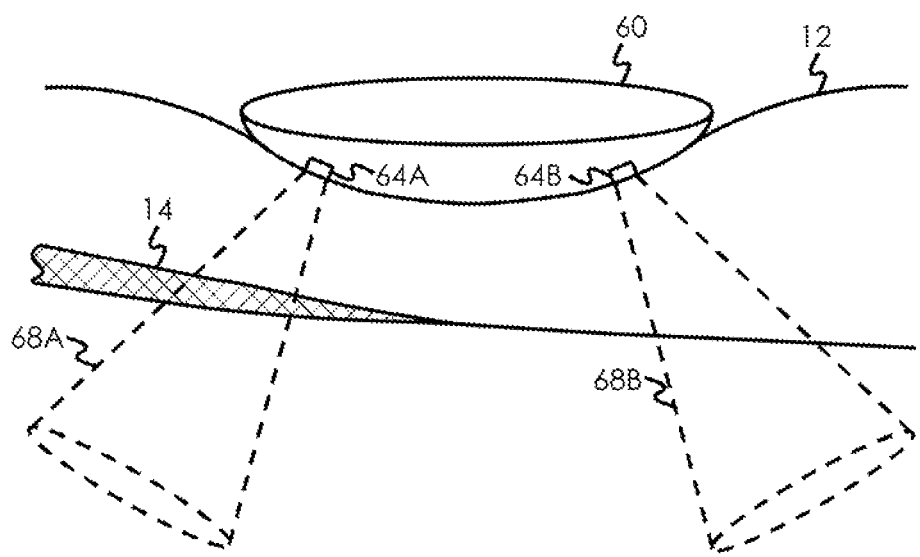
FIG. 8 is an illustration showing a closed artery beneath the alternate effector of FIG. 7 and the scanning regions of ultrasound transducers that form part of the effector.

FIG. 8 depicts alternate effector 60 in cross-section applying pressure to body surface 12. Effector 60 is positioned on the body surface above an artery 14 that is to be closed by effector 60. In FIG. 8 the tissue region insonified by transducer 64A is indicated by dashed line 64A and the tissue region insonified by transducer 64B is indicated by dashed line 64B. When effector 8 is initially applied to the body surface controller 2 operates to identify the transducers on the front face of effector 8 that are detecting blood flow and to determine if blood is flowing past effector which is indicated by blood flow being detected by transducers that are on substantially opposite sides of effector 8. In the example shown in FIG. 8, prior to artery 14 being closed by effector 60 blood flow in the artery was detected by both transducer 64A and transducer 64B.

To apply the minimum pressure necessary to stop blood flow past effector 60 controller 2 operates to increase the pressure applied by effector 60 to the body surface until blood flow is no longer detected in the region insonified by transducer 64B and blood flow remains detectable in the region insonified by ultrasound transducer 64A, as shown in FIG. 8. When artery 14 is closed by effector 60 the movement of blood in the proximal portion of the artery 14 insonified by transducer 64A continues with each cardiac cycle and is detectable by transducer 64A. If additional pressure is applied by effector 60 the distance that arterial blood penetrates beneath effector 60 will be decreased as described elsewhere above and the flow of blood in the proximal portion of the artery insonified by transducer 64A may no longer be detectable. Controller 2 may be configured to regulate the pressure applied by effector 60 near a level that permits blood flow in artery 14 to remain detectable by transducer 64A while not being detectable by transducer 64B.

The tourniquet effector system described above estimates and indicates the pressure gradients produced on the surface of the body by an effector, thereby allowing the pressure gradients to be minimized. The system also detects and monitors blood flow beneath the effector, thereby allowing the pressure applied by the effector to be regulated near the minimum necessary to stop blood flow past the effector.

The invention claimed is:

1. A tourniquet effector for applying pressure to a body through which arterial blood flows, comprising:
    an effector having a back face and a front face that includes at least two pressure sensors;
    a fixture structure for supporting the effector adjacent to a surface on the body;
    an actuator attached between effector back face and the fixture structure, the actuator being movable and controllable for advancing the effector to press the effector front face against a contact area on the body surface at a particular orientation of the front face relative to the contact area;
    wherein the pressure sensors produce a pressure signal indicative of the pressure applied by the front face to the contact area; and
    a controller for controlling the actuator, the controller being in communication with the pressure sensors for receiving the pressure signal, the controller operable for estimating and indicating a pressure gradient in the body that is produced by the front face of the effector when pressed against the contact area of the body surface, whereby the pressure gradient is a rate of change of pressure across a distance in the body.

2. The tourniquet effector of claim 1 wherein the front face has a perimeter that defines the contact area on the body surface against which the front face is pressed, the front face being configured so that no pressure is applied by the effector outside of the perimeter of the front face and so that the front face does not surround the body.

3. The tourniquet effector of claim 1 wherein the front face is generally convex shaped to thus reduce the pressure gradient.

4. The tourniquet effector of claim 1 wherein the front face shape is changeable, thereby to change the pressure gradient when the front face is pressed against the contact area of the body surface.

5. The tourniquet effector of claim 1 wherein the actuator is a linear actuator.

6. The tourniquet effector of claim 1 wherein the actuator is movable in more than one degree of freedom, thereby enabling the actuator to advance the effector to press the effector front face against a contact area on the body surface at any one of a plurality of particular orientations of the front face relative to the contact area 7. The tourniquet effector of claim 1 wherein the at least two pressure sensors are spaced apart from each other at locations on the front face and producing pressure signals indicative of the pressure applied by the front face to the contact area at the locations of the sensors, and wherein the controller is in communication with the sensors for receiving the pressure signals, and for estimating and indicating the pressure gradient produced by the front face of the effector when pressed against the contact area of the body surface.

8. The tourniquet effector of claim 7 wherein the controller employs data relating to the shape of the front face for estimating and indicating the pressure gradient.

9. The tourniquet effector of claim 7 wherein the controller employs data relating to the particular orientation of the front face for estimating and indicating the pressure gradient.

10. The tourniquet effector of claim 1, further comprising a transducer communicating with the controller and arranged for determining a distance of penetration of blood flow in an artery that underlies the front face.

11. The tourniquet effector of claim 10 wherein the controller controls the actuator for advancing the front face based upon the distance of penetration of blood flow in an artery underlying the front face as determined by the transducer.

12. The tourniquet effector of claim 11 wherein the transducer comprises a two-dimensional ultrasonic array.

13. A tourniquet effector for stopping arterial blood flow in a body, comprising:
- an effector having a front face sized to overlie an artery in a region of the body and having a predetermined area, the effector also having a back face;
- actuation means for applying force to the back face to position the effector front face at a surface of the body to overlie the artery and for applying the effector front face to the body surface with a level of pressure sufficient to stop blood flow in the artery;
- pressure sensors mounted at the front face for estimating at least two levels of pressure applied by the effector front face to at least two locations between which is defined a distance across the body surface; and
- means for communicating with the sensors and for producing a user-perceptible indication of a pressure gradient, wherein the pressure gradient is a rate of change of pressure across a distance in the body.

14. The tourniquet effector of claim 13 wherein the shape of the tourniquet effector front face is changeable, thereby to enable changes in the pressure gradient.

15. The tourniquet effector of claim 13 further comprising:
- transducer means for detecting a distance of penetration of blood flow in the artery;
- control means communicating with the transducer means for controlling the actuation means for pressing the effector front face against the surface with a pressure sufficient to maintain the distance of penetration of blood in the artery near a selected distance of penetration.

* * * * *